United States Patent
Pelssers et al.

(10) Patent No.: US 10,680,162 B2
(45) Date of Patent: Jun. 9, 2020

(54) STIFFNESS CONTROL FOR ELECTROACTIVE ACTUATORS

(71) Applicant: KONINKLIJKE PHILIPS N.V., Eindhoven (NL)

(72) Inventors: Eduard Gerard Marie Pelssers, Panningen (NL); Petrus Cornelis Hendriks, Eindhoven (NL); Franciscus Johannes Gerardus Hakkens, Eersel (NL); Achim Hilgers, Alsdorf (DE); Daan Anton Van Den Ende, Breda (NL); Mark Thomas Johnson, Arendonk (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/347,610

(22) PCT Filed: Nov. 10, 2017

(86) PCT No.: PCT/EP2017/078968
§ 371 (c)(1),
(2) Date: May 6, 2019

(87) PCT Pub. No.: WO2018/087342
PCT Pub. Date: May 17, 2018

(65) Prior Publication Data
US 2019/0348596 A1    Nov. 14, 2019

(30) Foreign Application Priority Data
Nov. 14, 2016   (EP) .................................... 16198639

(51) Int. Cl.
*H01L 41/09*    (2006.01)
*H01L 41/04*    (2006.01)
(Continued)

(52) U.S. Cl.
CPC ..... *H01L 41/0926* (2013.01); *A61M 25/0158* (2013.01); *F03G 7/005* (2013.01);
(Continued)

(58) Field of Classification Search
CPC .. H01L 41/0926; H01L 41/183; H01L 41/042
(Continued)

(56) References Cited

U.S. PATENT DOCUMENTS 6,703,761 B2 * 3/2004 Gallmeyer ............ H01L 41/042
310/316.01
7,586,238 B2 * 9/2009 Liu .................... H01H 59/0009
310/309

(Continued)

OTHER PUBLICATIONS

Bryan E. Schubert and Dario Floreano, 2013, Variable stiffness material based on rigid lowmelting-point-alloy microstructures embedded in soft poly(dimethylsiloxane) (PDMS), Royal Society of Chemistry Adv.,3 , 24671-24679.
(Continued)

*Primary Examiner* — An H Do
(74) *Attorney, Agent, or Firm* — Schott, P.C.

(57) ABSTRACT

An actuator device is provided having a controllable stiffness profile, wherein an actuator member (12) comprises an electroactive polymer material (16) having light absorbing filler elements (20) embedded therein. The filler elements are adapted to absorb and convert incident light (26) to heat energy to therefore heat surrounding sections of the electroactive material. By selectively controlling an intensity level or spectral composition of a light source (24) directed at the actuator member, a specific degree and spread of heating can be achieved across the member and, as a result, a specific desired stiffness or flexibility profile can be realised across the actuator member.

20 Claims, 6 Drawing Sheets

(51) Int. Cl.
*H01L 41/18* (2006.01)
*A61M 25/01* (2006.01)
*F03G 7/00* (2006.01)
*A61M 25/00* (2006.01)
*A61M 25/09* (2006.01)

(52) U.S. Cl.
CPC .......... *H01L 41/042* (2013.01); *H01L 41/183* (2013.01); *A61M 2025/0058* (2013.01); *A61M 2025/09175* (2013.01)

(58) Field of Classification Search
USPC ...................... 347/68–70; 310/309, 330, 341
See application file for complete search history.

(56) References Cited

U.S. PATENT DOCUMENTS

| | | | |
|---|---|---|---|
| 7,598,651 B2* | 10/2009 | Kornbluh | B64C 3/48 310/309 |
| 8,237,324 B2 | 8/2012 | Pei et al. | |
| 9,119,737 B2 | 9/2015 | Mertens et al. | |
| 2002/0175594 A1 | 11/2002 | Kornbluh et al. | |
| 2004/0143160 A1 | 7/2004 | Couvillon | |
| 2006/0069346 A1 | 3/2006 | Smith et al. | |
| 2007/0112331 A1 | 5/2007 | Weber et al. | |
| 2007/0250036 A1 | 10/2007 | Volk et al. | |
| 2008/0185936 A1 | 8/2008 | Panchapakesan et al. | |
| 2009/0157048 A1 | 6/2009 | Sutermeister et al. | |
| 2010/0297334 A1 | 11/2010 | Weber | |
| 2013/0328440 A1 | 12/2013 | Kornbluh et al. | |
| 2014/0333992 A1 | 11/2014 | Wagemans et al. | |
| 2016/0049576 A1 | 2/2016 | Levatich et al. | |
| 2018/0138833 A1* | 5/2018 | van den Ende | H02N 2/062 |

OTHER PUBLICATIONS

C. Liu,a H. Qinb and P. T. Mather, 2007, "Review of progress in shape-memory polymers", J. Mater. Chem., 17, 1543-1558.

Markus Henke—Gerald Gerlach, 2014, On a high-potential variable-stiffness device, Microsyst. Technol., 20:599-606.

Henke, M. et al. 2012, "Multi-layer beam with variable stiffness based on electroactive polymers", Electroactive Polymer Actuators and Devices (EAPAD) 2012, edited by Yoseph Bar-Cohen, Proc. of SPIE vol. 8340.

Ren, Z. et al., 2016, "Phase-Changing Bistable Electroactive Polymer Exhibiting Sharp Rigid-to-Rubbery Transition", Macromolecules, 49, 134-140.

Karl Kruusamae, 2015, "Electroactive Shape-Fixing of Bucky-Gel Actuators", IEEE/ASME Transactions on Mechatronics, vol. 20, No. 3, Jun. 2015, 1108.

Carpi et al "Dielectric Elastomers as Electromechanical Transducers: Fundamentals, Materials, Devices, Models and Applications of an Emerging Electroactive Polymer Technology" Oxford, Elsevier, p. 53 (2011).

Yao Y et al; "'Two way' shape memory composites based on electroactive polymer and thermoplastic membrane", Composites Part A: Applied Science and Manufacturing,vol. 90, Aug. 18, 2016 (Aug. 18, 2016), pp. 502-509.

Hu W et al: "New Dielectric Elastomers with Variable Moduli",Advanced Functional Materials, vol. 25, No. 30, Aug. 2015 (Aug. 2015),pp. 4827-4836.

International Search Report and Written Opinion dated Mar. 1, 2018.

S. Smiya "Handbook of Advanced Ceramics: Materials, Applications, Processing and Properties" Nonlinear Dielectricity of MLCC's Waltham Academic Press, 2013 p. 415.

* cited by examiner

STIFFNESS CONTROL FOR ELECTROACTIVE ACTUATORS

CROSS-REFERENCE TO PRIOR APPLICATIONS

This application is the U.S. National Phase application under 35 U.S.C. § 371 of International Application No. PCT/EP2017/078968, filed on Nov. 10, 2017, which claims the benefit of EP Patent Application No. EP 16198639.3, filed on Nov. 14, 2016. These applications are hereby incorporated by reference herein.

FIELD OF THE INVENTION

This invention relates to an actuator device having controllable stiffness and in particular to an electroactive material based actuator member having controllable stiffness.

BACKGROUND OF THE INVENTION

Electroactive materials (EAMs), and in particular electroactive polymers (EAPs) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP materials give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes). Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimensionwise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

FIGS. 1 and 2 show two possible operating modes for an EAP device.

The device comprises an electroactive polymer layer 8 sandwiched between electrodes 4, 6 on opposite sides of the electroactive polymer layer 8.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 10. A voltage is used to cause the electroactive polymer layer to curve or bow.

Together, the electrodes, electroactive polymer layer, and carrier may be considered to constitute the overall electroactive polymer structure.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

An electroactive polymer structure as described above may be used both for actuation and for sensing. The most prominent sensing mechanisms are based on force measurements and strain detection. Dielectric elastomers, for example, can be easily stretched by an external force. By putting a low voltage on the sensor, the strain can be measured as a function of voltage (the voltage is a function of the area). Another way of sensing with field driven systems is measuring the capacitance-change directly or measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

Possible applications for EAP based actuators/sensors are widespread. To further improve the versatility and range of applications for this technology, it would be desirable to improve the range of actuation displacements and forces achievable by EAP actuators. It would furthermore be desirable to improve the capacity of EAP actuators to perform more complex movements and shape-changing effects, including for instance multi-jointed actuation motions. Such effects are currently only achievable using EAP matrices or segmented EAP structures, which are complex to construct and more expensive to manufacture.

EAP actuators offering improved actuation function would therefore be desirable.

SUMMARY OF THE INVENTION

It has been realised by the inventors that the range of motions and forces achievable in a single EAP structure may be improved in the case that a greater degree of control were possible over the stiffness of the structure. Stiffness control within EAP actuators is presently highly limited in the state of the art, extending at most to selective alternation between two different binary states of material flexibility.

EAPs intrinsically exhibit a degree of stiffness variation, arising as a result of the compression incurred within the material upon electrical stimulation. The effect however is relatively small (for example a stiffness variation factor of only 5 or 6 with a pre-strained actuator) and furthermore the stiffness change is directly related to the actuator deformation.

It would be desirable to achieve an electroactive polymer based actuator having a stiffness (e.g. Young's or storage modulus) which can vary over at least an order of magnitude, and which is controllable by a stimulus independent of the electrical stimulus used to control actuation of the EAP.

Such independently controllable stiffness would enable the EAP actuator to cover a much broader range of forces and displacements than is presently possible with constant stiffness devices. Furthermore, it would be possible to provide devices having variable stiffness and damping profiles, or offering complex (array light) shape changing effects; functionality which is currently only possible using matrices or by means of segmented electroactive polymer structures.

It has been known to temporarily adjust the stiffness of an EAP actuator between two different levels in order to facilitate bi-stable functionality. U.S. Pat. No. 8,237,324 for example discloses heating an electroactive polymer transducer from below its glass transition temperature to above its glass transition temperature in order to enable easy deformation by means of electrical stimulation. Once deformation of the actuator has been achieved, the actuation is made stable by once again cooling the actuator to below its glass transition temperature. It is disclosed that light absorbing particles may in some examples be used to assist in the heating process.

Such methods however offer only a limited degree of control over the stiffness of the EAP actuator, the states achievable being related in particular to the problem to improving the bi-stability of the actuator structure. Only two states of stiffness are achievable, correspondent with the two phases of the material, below and above the glass transition temperature.

Devices and methods for providing enhanced degree of control over a stiffness of an EAP actuator are therefore required.

The invention is defined by the claims.

According to an aspect of the invention, there is provided an actuator device, having an adjustable stiffness profile comprising:
  an actuator member, comprising:
    an electroactive material, adapted to deform in response to application of an electrical stimulus; and
    light absorbing filler elements within the electroactive material, adapted to absorb and convert incident light energy to heat energy;
  a controllable light source, optically coupled with the actuator member, and operable to provide a light output onto the actuator member, the light output being controllable between a range of different intensity levels and/or spectral compositions so as to controllably adjust a stiffness profile of the actuator member; and a controller operable to control the intensity level and/or spectral profile of the light output so as to selectively realise in the actuator member any of a range of at least three different stiffness profiles.

Embodiments of the invention thus provide an EAM actuator having a stiffness which is controllable by means of a luminous stimulus. By varying the intensity and/or spectral profile of a light output directed onto the actuator member, the stiffness profile exhibited across the actuator member may be precisely controlled.

The light absorbing fillers are configured with the property of absorbing light and efficiently converting this to heat energy, the heat energy then being radiated or conducted outward from the fillers to the electroactive polymer material surrounding them. As the electroactive polymer material heats, its stiffness steadily declines, the change in stiffness being directly dependent upon the temperature change induced.

Irradiance of the light absorbing fillers therefore provides an efficient and precisely controllable means for altering the stiffness of the electroactive material, via the mechanism of luminously stimulated heating. Heating using luminously sensitive fillers offers a much more efficient and controllable means for heating than for example typical conductive-based methods (using for instance attached heating elements or strips). The fillers are embedded within the electroactive material, and hence are able to deliver 100% of their generated heat to the material itself, without any (at least initial) loss the ambient environment. Furthermore, using embedded fillers, it is possible (in accordance with at least some examples) to selectively control heating of only certain portions or sections of the EAM layer and not others. This is far more difficult using external conduction based methods. Greater control of the heating leads to greater control over the stiffness.

The electroactive material functions as a supporting matrix within which the filler, such as small particles, is embedded.

The intensity level of the light refers broadly to a luminous output power or level of the light, and does not necessarily refer to any specific physical quantity. It may, by way purely of example, refer to any of: a luminous flux, luminous power, radiant flux of the emitted light, radiant intensity, luminous intensity, luminosity, irradiance, luminance or radiance.

The spectral composition refers to the composition of the light in terms of its component wavelengths or frequencies. It may be interpreted as referring for instance to an emission spectrum of the controllable light source.

The stiffness profile may refer to a level or degree of stiffness exhibited uniformly across the actuator member. Alternatively, the stiffness profile may refer to a spatial stiffness profile, which varies locally across the extent of the actuator member.

The term stiffness furthermore is to be interpreted broadly as referring generally to the property of flexibility or rigidity or elasticity of a material. It does not necessarily refer to any physical quantity in particular. However, in particular examples, it may cover for instance a Young's modulus or storage modulus of a material.

In accordance with one or more embodiments, the controller may be operable to control the intensity level and/or spectral profile of the light output so as to realise in at least a portion of the actuator member any of a continuous spectrum of stiffness levels. The intensity level for example might be controllable across a continuous spectrum of intensity values. The stiffness level of at least a portion of the actuator member may be directly dependent upon the intensity of incident light. The controller may therefore be operable to achieve any of a continuous spectrum of stiffness levels by selectively controlling the output intensity of the light source so as to emit light of an intensity known to be correspondent with a given desired stiffness level in the material.

In accordance with any embodiment of the invention, the controller may be configured to selectively control the stiffness profile realised in the actuator member on the basis of a pre-defined control schedule and/or on the basis of one or more input control parameters. The controller may for example comprise program instructions, the program instructions when executed on the controller causing it to carry out steps of a particular control schedule or program. The control schedule or program may for example include cycling through a series of different stiffness profiles of the actuator member by means of controlling the light source to cycle through a series of different output levels or modes, each correspondent with a particular desired stiffness profile of the actuator member. The predefined control schedule may in examples include steps being dependent upon one or more input parameters. The input parameters may in examples include user input commands or parameters. In further examples, the input parameters may be parameters obtained by means of one or more sensor devices, for example temperature sensors or rigidity sensors.

In accordance with one or more embodiments, the light-absorbing elements may be non-homogenously distributed in the electroactive polymer, so as to enable realising of spatially non-uniform stiffness profiles in the actuator member. For example, the light absorbing filler elements may be distributed in a set of spatially discrete concentrations of filler elements.

By providing in the actuator member spatially concentrated clusters of light absorbing fillers, locally varying stiffness changes can be achieved. In particular, in those locations in which there are larger concentrations of EAP fillers, a greater degree of heating will typically occur (upon irradiating the actuator member with a uniform spread of light) than in those locations in which there are lower concentrations of filler particles.

The higher concentration areas will as a result exhibit a greater degree of stiffness change than the low concentration areas, the higher concentration areas becoming more flexible relatively compared to the low concentration areas. In this way the non-homogenous spatial distribution of filler elements may lead to inducement of non-spatially homogenous stiffness profiles across the actuator member.

In accordance with one or more embodiments, the actuator member may comprise a plurality of different locally concentrated groups of light absorbing filler elements, each group being adapted to absorb light of a different range of wavelengths, and wherein the controller is configured to control the spectral composition of the light output in accordance with a defined control schedule, in order to realise a particular stiffness profile of the actuator member.

In particular, the controller may be configured to control the light output so as to comprise wavelengths of light to which only a subset of the groups of filler elements are sensitive. In this way, the controller may selectively stimulate heating of only certain regions or sections of the actuator member and thereby realise a particular desired stiffness profile correspondent with this pattern of heating.

The controller accordingly may be configured to selectively control local stiffness of the actuator member at one or more regions of the member by selectively including or excluding wavelengths of light to which filler elements included said one or more regions are sensitive.

In accordance with one or more embodiments, the actuator device may comprise a stacked arrangement of multiple different planar concentrations of filler elements, being stacked along an axis extending parallel to an optical axis of the light output, and wherein each planar concentration is adapted to absorb a different portion of a spectral composition of the light output. The stack of planar concentrations effectively forms a layer stack, each layer being populated by filler particles absorptive of a different set of wavelengths of light.

Each of the planar concentrations may for example be adapted to absorb so-called subtractive colours of a white light source. For example, each of a stack of three planar concentrations may be adapted to absorb cyan, magenta, and yellow light respectively. In this way, only the cyan portion of a white light source falling incident on the first planar layer would be absorbed, with the magenta and yellow light portions being transmitted through to the remaining two layers situated beneath. The magenta portion may then be absorbed by the second layer, with yellow light transmitted to the third layer.

The composition of the light could be adjusted in accordance with which of the layers are desired to be stimulated. For example the light source may comprise only cyan and yellow light so that the middle layer is not stimulated.

In this way, selective heating of two or more planar element concentrations stacked atop one another may be achieved through illumination of only one side of the stack.

In accordance with one or more embodiments, the controllable light source and the actuator member may be optically coupled by means of an elongate light guide, and optionally said elongate light guide may be an optical fibre.

In accordance with any embodiment of the invention, the light absorbing filler elements may comprise filler elements formed of at least one of:
 a black pigment;
 a transition metal;
 a wavelength-specific dye;
 a phosphor; and
 a fluorophore.

In accordance with one or more embodiments, the light absorbing filler elements may comprise a material having a temperature-dependent optical transmittance, such that optical transmittance plateaus at a particular temperature, and optionally wherein the optical transmittance plateaus for temperatures above a glass transition temperature of the electroactive polymer material.

Examples in accordance with a further aspect of the invention provide an elongate probe having a steerable section, the elongate probe comprising one or more of any of the actuator devices described above for facilitating steering of said steerable section. The elongate probe may in particular examples be a catheter or a guide wire. The actuator members of the actuator devices may in examples be included or embedded in walls of the elongate probe so as to facilitate steering of the tip. In particular examples, the elongate probe may comprise a plurality of the actuator devices. In these cases, optionally, two or more of the actuator devices may share a single controller.

In accordance with one or more embodiments, the elongate probe may comprise a pair of opposing actuator members for steering the steerable section, a stiffness of the two members being reciprocally controlled such that upon steering in any given direction, a mechanically active one of the two members is controlled to have a high stiffness, for enabling a strong active actuation force, and a mechanically passive one of the two members is controlled to have a low stiffness, for ensuring minimum resistance to the actuation force.

In particular examples, the elongate probe may comprise a dedicated light guide for each actuator member, for providing a separately controllable light output to each actuator member.

Examples in accordance with a further aspect of the invention also provide a method of selectively controlling a stiffness profile of an actuator member, the actuator member comprising:
 an electroactive material, adapted to deform in response to application of an electrical stimulus, and
 light absorbing filler elements within the electroactive material, adapted to absorb and convert incident light energy to heat energy,
 the method comprising:
 directing a light output onto the actuator member, the light output having a controllable intensity level and/or spectral composition; and
 controlling the intensity level and/or spectral profile of the light output so as to selectively realise in the actuator member any of a range of at least three different stiffness profiles.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an electroactive material actuator device having a controllable stiffness profile. An actuator member of the device comprises an electroactive material such as an electroactive polymer having light absorbing filler elements embedded or contained therein. The light absorbing filler elements are adapted to absorb and convert incident light energy to heat energy to therefore heat surrounding sections of the EAP material. By selectively controlling an intensity level or spectral composition of a light source directed at the actuator member, a specific degree and spread of heating can be achieved across the member and, as a result, a specific desired stiffness or flexibility profile realised across the body of the actuator member.

Figure 1:
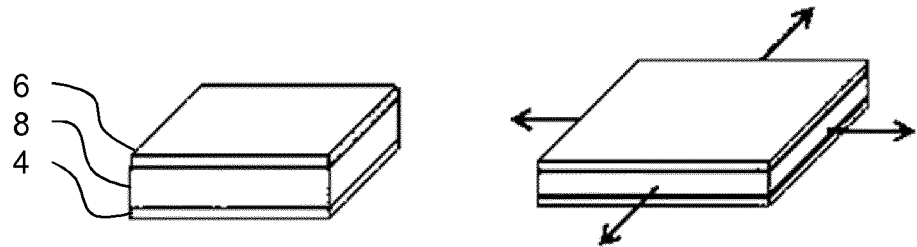
FIG. 1 shows a known electroactive polymer device which is not clamped.
Figure 2:
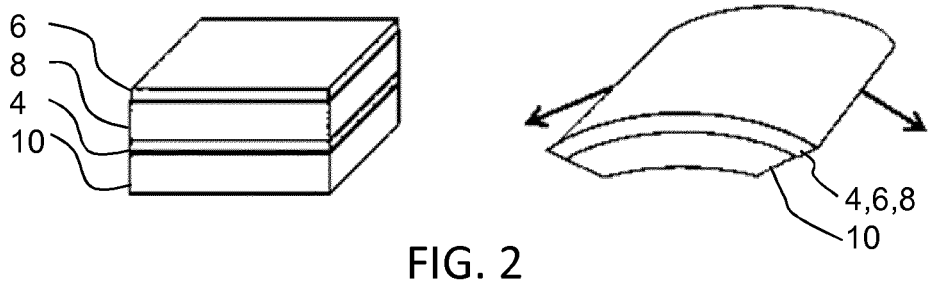
FIG. 2 shows a known electroactive polymer device which is constrained by a backing layer.
Figure 3:
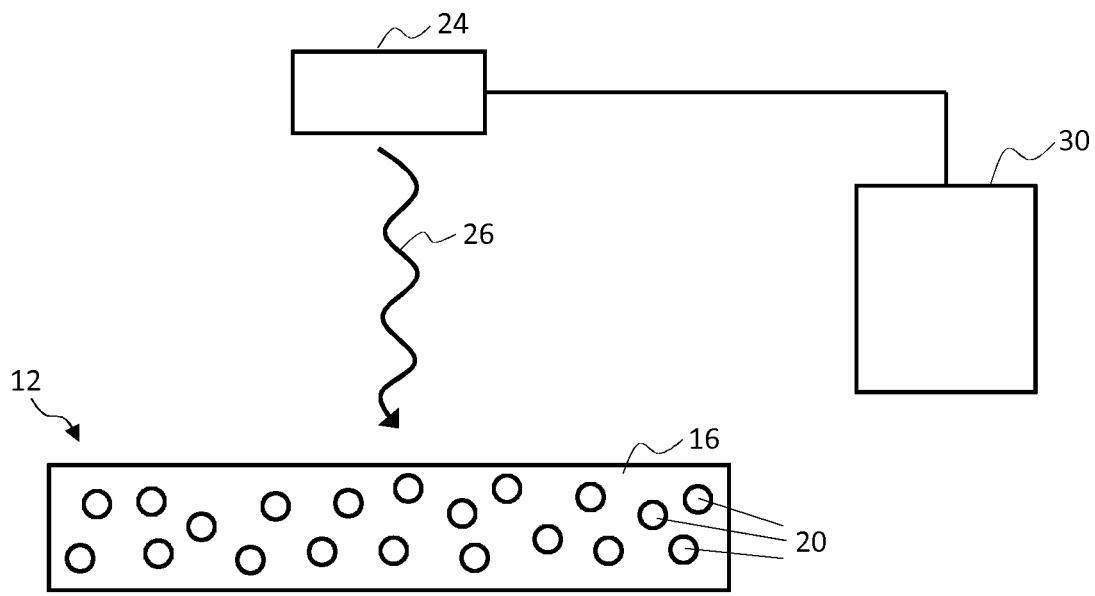
FIG. 3 schematically illustrates a first example actuator device in accordance with one or more embodiments of the invention.

FIG. 3 schematically illustrates a simple first example of an actuator device in accordance with one or more embodiments of the invention. The actuator device comprises an actuator member 12 being formed of an electroactive polymer material 16, and a plurality of light absorbing filler elements 20 within the electroactive polymer material. The device further comprises a controllable light source 24 operable to direct a light output 26 onto the actuator member 12.

Although in the simple illustration shown in FIG. 3, the light source 24 is arranged so as to directly provide the light output 26 onto a surface of the actuator member 12, in alternative examples the light source and actuator member may be indirectly optically coupled by means for example of a suitable light guide configured for carrying the light output between the light source and the actuator member.

The actuator device further comprises a controller 30, operatively coupled with the controllable light source 24, and operable to control the intensity level and/or spectral profile of the light output 26 emitted by the light source.

Figure 4:
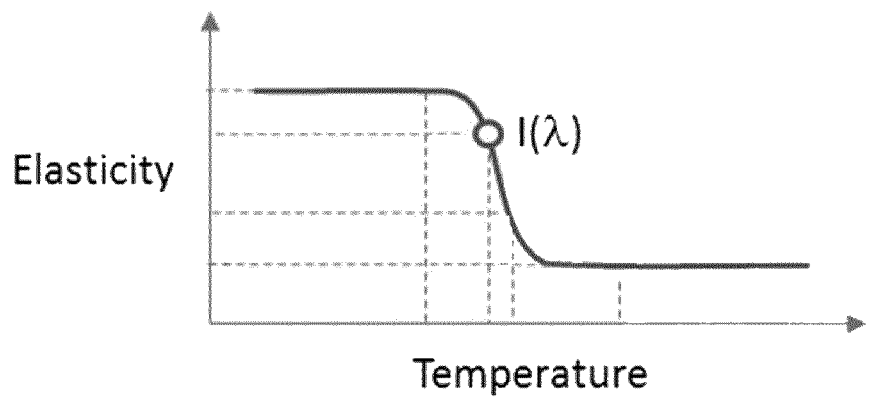
FIG. 4 shows a graph illustrating the relationship between elasticity and temperature for a typical electroactive polymer material.

The light absorbing filler elements 20 are formed of material having the property of absorbing incident light and converting the light to heat energy. The generated heat energy is then dissipated from the filler elements outwards into the surrounding electroactive polymer material of the actuator member 12. The light absorbing fillers convert light to heat in an efficient and controlled way, such that the temperature of the composite EAP material in the actuator member reaches a stable value quickly and in a controlled way. The particular temperature achieved and the time taken to reach this temperature depends upon the type and amount of filler material, and also the ratio of filler material to EAP material in the actuator member. It can furthermore be controlled by means of the intensity or the spectral composition of the light output 26 directed onto the actuator member. The rigidity or stiffness of the actuator member is dependent upon its temperature. This is shown in FIG. 4 which provides a graph illustrating a typical relationship between temperature and elastic or storage modulus for an electroactive polymer material. The relationship holds both for a number of field driven and ionic driven EAP materials As shown, the elastic modulus remains fairly constant for a certain range of temperatures. At a particular temperature (in most cases a glass transition temperature), the elastic modulus begins to decrease at a relatively fast rate in dependence upon increasing temperature. At a further, higher, temperature, the elastic modulus of the material stabilises; with further increases in temperature not effecting significant further changes in elasticity.

By way of example, EAP materials with a (glass) transition temperature in the range of 0-40° Celcius include: poly(t-butyl acrylate), poly(vinylidene fluoride-co-hexafluoropropylene), polyurethane and P(VDF-TrFE-CFE) blended with PMMA. These represent one set of illustrative examples of suitable materials which might be particular applicable in typical (room temperature) environments. This list is not exhaustive and other suitable materials (examples of which will be apparent to the skilled person) may also be used.

By controlling the quantity and rate of luminous energy directed onto the actuator member 12, a precise degree of heating of the actuator member can be regulated, and as a result a level of rigidity of the member controlled.

The controller 30 may in examples be operable to control an intensity level of the light output 26. The 'intensity level' may, by way of example, refer to a luminous power of the light output 26. By controlling the intensity level of the light output, a rate of energy transfer between the light source 24 and the light absorbing filler elements 20 may be controlled. By controlling the rate of energy transfer, a rate of warming of the actuator member induced by conversion of the light energy to heat energy in the light absorbing filler elements may accordingly be controlled. In this way the controller 30 is operable, via control of the controllable light source 24, to precisely control a state of stiffness of the actuator member.

In examples, the intensity level may be controllable across a continuous spectrum of different intensity levels. In accordance with these examples, a continuous spectrum of different stiffness levels may be achievable within the actuator member in dependence upon the intensity level of the light output generated by the light source 24.

The actuator device offers numerous advantages compared with prior art devices. In particular, the stiffness of the actuator member is controllable across a range of different levels. In particular the controller 30 is operable to selectively realise in the actuator member any of a range of at least three different stiffness profiles. In the particular example of FIG. 3, the stiffness profiles may refer to different stiffness levels of the actuator member, where each stiffness level corresponds with a particular intensity level of the generated light output 26.

Furthermore, examples of the present invention enable the stiffness to be controlled independently from the actuation state of the member 12. The stiffness can be fully controlled by adjustments in the light output 26 of the light source 24, which is entirely independent of the electrical stimulation used to control actuation of the actuator member 12.

In addition, in examples of the present invention, the heat used to alter the stiffness of the actuator member is generated within the material of the member itself. The efficiency of heat transfer is therefore significantly improved compared for instance to alternative heating means such as for example providing externally applied heating elements or other heat conduction devices.

Examples of the present invention allow elasticity of the electroactive polymer material to be varied by a factor of more than 10, significantly greater than stiffness variations achievable intrinsically by means of mechanical deformation of the material for instance.

In accordance with one or more examples, the controller 30 may be configured to selectively control the stiffness profile achieved in the actuator member on the basis of a predefined control schedule. The predefined control schedule may in examples comprise steps or processes dependent upon one or more input parameters. The input parameters may be user input parameters or may be input parameters obtained for instance from one or more sensor devices such as a temperature sensor thermally coupled with the actuator member.

By way of simple example, the controller may for instance be configured to implement a control schedule wherein the light source 24 is controlled to emit a light output 26 sufficient for creating in the actuator member 12 one of a set of at least three different stiffness profiles. The control schedule may for example comprise for each of the possible stiffness profiles a particular light intensity and/or spectral composition which is known to be sufficient for realising the particular stiffness profile. The controller 30 may for instance comprise a memory in which are stored for each of the possible stiffness profiles a corresponding set of luminous properties for the light output which are necessary to achieve that profile within the actuator member.

The control schedule may for instance include a step or process of obtaining or seeking a user input command, the user input command being indicative of a particular one of the at least three stiffness profiles which the controller is operable to effect within the actuator member. The control command(s) may be provided to the controller 30 by means for example of a separately provided user interface device. Alternatively, a suitable user interface device may be comprised by the actuator device.

Additionally or alternatively, in accordance with one or more examples the controller 30 may be configured to execute a control schedule which comprises steps for cycling the actuator member 12 through a series or progression of different stiffness profiles. The series of different stiffness profiles may be consecutive profiles along a continuous spectrum of profiles (for instance different uniform stiffness levels along a continuous spectrum of possible stiffness levels). Alternatively, the different stiffness profiles may be discrete profiles, for instance comprising stimulation of different sets of local regions within the actuator member 12 to thereby realise different stiffness configurations or different shape change effects.

The light absorbing filler elements may in examples comprise filler particles or pellets. The combination of the EAP material and embedded filler particles may form an EAP composite material. In particular examples, the EAP filler elements may comprise black pigments. Black pigments may be suitable for use in combination with a relatively intense light output 26. The black colouring of the pigments gives them a high absorption efficiency, therefore improving the efficiency of energy transfer between the light source 24 and the actuator member 12. Suitable black pigments include, by way of non-limiting example, Acetylene black, Antimony black, Logwood Black lake (color index: NBk2), and Aniline Black (PBk1). A wide variety of alternative black pigments also exist, and any suitable pigment may alternatively be used.

The pigments should preferably be non-conducting so as to avoid electrical shortcut or breakdown. Additionally, pigments should preferably be insoluble.

Dyes may also be considered. Dyes are typically not universally insoluble (they dissolve in some solvents), but are insoluble with respect to certain groups of solvents. When insoluble, dyes become dispersed as particles (similar to pigments) within the electroactive material matrix. Suitable examples include (by way of non-limiting example only) Indian ink, Black 7984.

In alternative examples, fillers may be used which comprise or are based on transition metals. Transition metal-based compounds also offer a high absorption efficiency and also high efficiency of heat generation within the surrounding EAP material. Suitable transition metal compounds may include nickel or copper oxides.

Additionally or alternatively, the light absorbing filler elements 20 may include wavelength specific dies such as phosphors or fluorophores. These materials typically have the property of absorbing only light of a particular set or spectrum of wavelengths. Inclusion of filler elements comprising such materials allows for wavelength specific absorption functionality in examples of the invention. In particular, by including for example different groups of filler elements, each adapted for absorption of a different set of wavelengths of light, more nuanced or locally directed control over a stiffness profile of the actuator member 12 may be realised by controlling the particular spectral composition of the light output 26 directed onto the actuator member 12.

The light may for instance be controlled to include only certain wavelengths of light and to exclude other wavelengths of light, in order thereby to selectively stimulate heating of only particular subgroups of the filler elements and thereby induce stiffness changes in only particular local regions of the actuator member.

Suitable phosphors for use in such examples include zinc sulphide or yttrium oxide based phosphors.

Suitable fluorophores for use in such examples include rhodamine based dyes.

The device makes use of composite materials which combine an electroactive material (in particular a polymer) and other particles (which will be termed generally as a "filler").

Means for manufacturing suitable EAP composite materials, comprising electroactive polymer material having embedded or contained filler particles will now be described, as well as the effects on the physical and electrical properties of the electroactive material.

The example of dielectric elastomer electroactive materials will first be presented. These are sandwiched between two electrodes to create dielectric electroactive polymer actuators. Silicone rubbers are the main applied elastomer group. The deformation is the result of attractive forces between the positively and negatively charged electrodes.

Compounding of particles in silicones is widely used on an industrial scale. As an example ultrasound transducer lenses are made of silicone (PDMS, Polydimethylsiloxane) filled with iron and silicon oxide particles to increase acoustic impedance and wear resistance. PDMS (silicone) compounds containing rutile ($TiO_2$) are widely used to increase the refractive index or to create white reflecting materials.

With respect to the performance of a dielectric electroactive polymer, compounding with non-conducting hard particles such as ceramics has two main significant effects. First, the stiffness of the material increases requiring larger forces to obtain the same strain levels. Another effect is that the dielectric constant of the composite changes (in general that of the filler will be higher than that of silicones, which is close to 3). Whether the strain effect depending on voltage is positive or negative depends on the dielectric constant of the particles and on particle size as more small particles have a larger effect on stiffness.

This is discussed in S. Somiya, "Handbook of Advanced Ceramics: Materials, Applications, Processing, and Properties," in Nonlinear Dielectricity of MLCCs, Waltham, Academic Press, 2013, p. 415. By way of example, adding particles increases the dielectric constant but also increases the stiffness.

Thus, compounding fillers into elastomers to influence the properties of a dielectric electroactive polymer is known. Adding high dielectric constant particles to increase the dielectric constant of the elastomer and therefore potentially the effectivity, has been widely investigated.

Silicone elastomers are in general prepared by mixing two components. One of them contains a Pt or peroxide curing catalyst. The different components can be mixed in a high speed mixer. In the same process, the filler can be added or the filler may already be premixed in one or both components. The filler material is in general applied in a solvent which evaporates during processing. After or during mixing in a high speed mixer in general vacuum is applied to remove air (and or solvents) inclusions. After this the mixture can be casted and cured. Curing temperature and time depends on the polymer grade but is typically around 80° C. for 10 minutes. Most particles are compatible with silicones as long as they do not inactivate the catalyst (for instance Sulphur containing materials). Peroxide curing silicones are less sensitive.

Silicones can be injection molded (liquid silicone rubbers, LSR). The two components are injected on a screw, after passing a (static) mixer, of the LSR injection molding machine. The filler particles may be pre-mixed in one or both components. The material is transported by a cold screw and injected into a hot mold where it cures fast depending on temperature. As the LSR has very low viscosity very thin sections can be realized. Typical curing temperatures are close to 180° C. and times around 30 seconds to one minute.

Besides casting and injection molding a number of other shaping technologies are available to produce silicon rubber compound components also in the form of thin films. Examples are extrusion (foils and profiles), rolling of foils, lamination and rolling of multilayers, doctor blade film casting, spin coating and screen printing.

The filling can be performed locally at the point of manufacture, for example by using multi shot injection molding (2 shot or over molding), silicone dispensing and over casting or silicone additive manufacturing (i.e. 3D printing)

The example of piezoelectric polymer composites will next be presented.

Piezo electric polymer composites containing a compound of PVDF (a matrix polymer) and ceramic particles such as PZT have been investigated. Manufacturing technologies like solvent casting and spin coating are suitable. Also, cold and hot pressing techniques are suitable. After dissolving the PVDF, evaporation of solvent until a viscous mix is obtained and mixing in the filler particles may then be performed. PVDF polymer based composites with a well dispersed grain size distribution and intact polymer matrix may be realized.

The example of relaxor electrostrictive polymer actuators will next be presented.

These are a class of semicrystalline terpolymers that can deliver a relatively high force with medium strain. Therefore these actuators have a wide range of potential applications. Relaxor electrostrictive polymers have been developed from "normal" PVDF polymers by employing proper defect modifications. They contain: vinylidene fluoride (VDF), trifluoroethylene (TrFE), and 1, 1-chlorofluoroethylene (CFE) or Chlorotrifluoro ethylene (CTFE).

Addition of defects in the form of chemical monomers, like 1, 1-chlorofluoroethylene (CFE) which are copolymerised with the VDF-TrFE, eliminate the normal ferroelectric phase, leading to a relaxor ferroelectric with electromechanical strain greater than 7% and an elastic energy density of 0.7 J/cm3 at 150 MV/m. Furthermore is has been described that by introducing defects via high electron irradiation of the P(VDF-TrFE) copolymers, the copolymer can also be converted from a "normal" ferroelectric P(VD-FTrFE) into a ferroelectric relaxor.

The materials may be formed by polymer synthesis as described in F. Carpi and et. al, "Dielectric Elastomers as Electromechanical Transducers: Fundamentals, Materials, Devices, Models and Applications of an Emerging Electroactive Polymer Technology," Oxford, Elsevier, 2011, p. 53. This discloses a combination of a suspension polymerization process and an oxygen-activated initiator. These films can be formed by pouring the solution on a glass substrate and then evaporating the solvent.

The desired filler can be added to the solvent before film casting. After casting, the composite can then be annealed to remove the solvent and increase crystallinity. The crystallization rate can reduce depending on filler concentration and particle size distribution. Stretching will align molecule chains and will become more difficult as particles can pin molecular chains. The dielectric constant will increase for most additives which reduces the required actuation voltage to reach a certain strain. The material stiffness will increase reducing strain.

The manufacturing process thus involves forming a polymer solution, adding particles, mixing, followed by casting (e.g. tape casting) potentially combined with lamination. Alternatives are spin coating, pressing etc.

Local variations in concentration can be realized using dispensing and or 3D solvent printing. Layer thicknesses between 10 to 20 μm are for example possible with 3D printing processes.

In all examples, the addition of the filler generally has an effect on the breakdown voltage. The maximum strain that can be reached with an electroactive polymer is determined by the maximum voltage that can be applied, which is the breakdown voltage (or dielectric strength).

The breakdown voltage of polymers is related to the dissociation of polymer molecules under an applied external field. The addition of filler particles in a polymer matrix can have a significant influence on the breakdown voltage. Especially larger particles can locally increase fields. Therefore compounding polymers with particles in the sub-micron range has a lower negative effect on voltage breakdown. Furthermore the polymer-filler interface structure can strongly influence voltage breakdown.

Agglomeration of particles is another effect that reduces breakdown voltage. However, by modifying particle surfaces, preventing agglomeration and improving the interface structure, the negative effect of voltage breakdown levels can be reduced. However, the filled polymers will obtain a lower breakdown strength than unfilled polymers, leading to lower actuation strain.

In conclusion, for dielectric electroactive polymers, compounding with particles can be achieved using a wide range of industrial compounding and shaping technologies. In order to keep the effect on stiffness and therefore stroke reduction for an actuator limited, smaller concentrations are preferred. For a given volume concentration, not too small particles are also preferred to keep the effect on stiffness limited. A soft base polymer can be selected to compensate for the rise in stiffness. Increased dielectric constant can enable actuation at reduced voltages. In order to maintain the dielectric strength, particle size and concentration should be limited and measures can be taken to improve the polymer-filler interface as well as particle dispersion. Local concentration variations can be achieved by printing a pattern of the filler particles.

For relaxor type electro active polymers compounding with particles is also possible. Similar trends with respect to the influence of particle concentration and size, on stiffness and dielectric strength are comparable to the effects described above. Particles can be added after polymerization. Dissolved polymers can be shaped using various technologies such as tape casting and spin coating. Also local concentration variations are possible for example by using a printing approach.

The light source may in accordance with one or more examples comprise one or more solid-state light sources such as LEDs or OLEDs. Additionally or alternatively, the light source may comprise other kinds of light source such as filament or fluorescent light sources. Additionally or alternatively, the light source may include one or more laser light sources.

It is noted that in describing embodiments of the present invention, control of the actuation state of the actuator member 12 is not described in any detail. The control of an electroactive polymer-based actuator for providing actuation effects is well-known and would be immediately recognised by the person skilled in the present field. For brevity therefore, control of the deformation of the actuator member through electrical stimulation is not described. Control of the actuation state of the actuator member may be implemented by means of a separate dedicated controller in particular examples. Alternatively, the single controller 30 may be configured to provide control over both of these aspects, but wherein, nonetheless, control of the stiffness is fully independent of control of the actuation state.

In the particular example illustrated in FIG. 3, the light absorbing filler elements 20 are distributed homogenously across the body of the actuator member 12. As a result, a uniform level of warming is induced within the actuator member in response to stimulation by the light output 26 (assuming the light output provides a uniform distribution of light energy across the actuator member). In this particular example therefore, changes in the light output 26 may effect changes in a uniform stiffness level across the actuator member.

Figure 5:
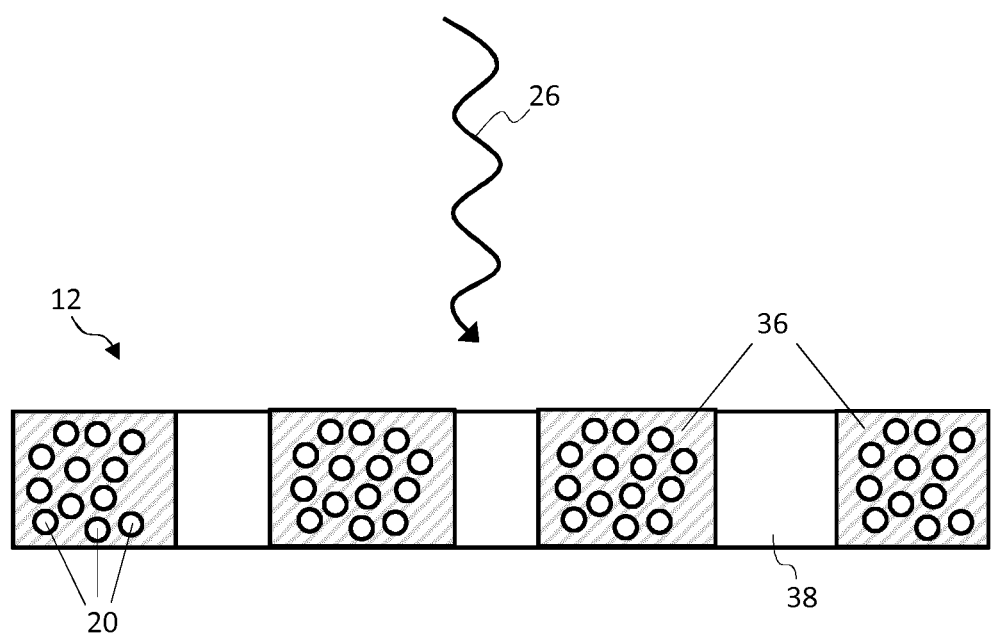
FIG. 5 schematically illustrates an actuator member of a second example actuator device in accordance with one or more embodiments.

In further examples however, the light absorbing filler elements 20 may be inhomogeneously distributed across the body of the actuator member 12. An example is shown in FIG. 5 which schematically illustrates an actuator member 12 in accordance with one or more embodiments of the invention, having filler elements 20 spatially clustered into locally concentrated groups. In accordance with this example, upon irradiating the actuator member 12 with the light output 26, only local regions comprising high concentrations of filler particles (schematically indicated by shaded regions 36) are stimulated to rise in temperature and thereby decrease in stiffness, while intermediate regions (schematically indicated by non-shaded areas 38) remain relatively un-heated and remain therefore at a higher level of stiffness.

As a consequence, a non-homogenous pattern of stiffness variation is induced across the body of the actuator member 12, wherein local regions become softer and more flexible while intervening regions remain rigid. The non-homogenous distribution of filler particles thereby enables stimulation of a non-homogenous stiffness profile across the actuator member in response to radiation by the light source 26.

In further examples, the clusters may be differently organised or arranged so as to provide a different pattern or profile of stiffness variation.

In accordance with one or more examples, the particles may not be distributed in discrete clusters as shown in FIG. 5, but rather may be distributed continuously across the actuator member but having a spatial distribution pattern which is non-homogenous, i.e. comprising higher concentration areas and lower concentration areas.

Figure 6:
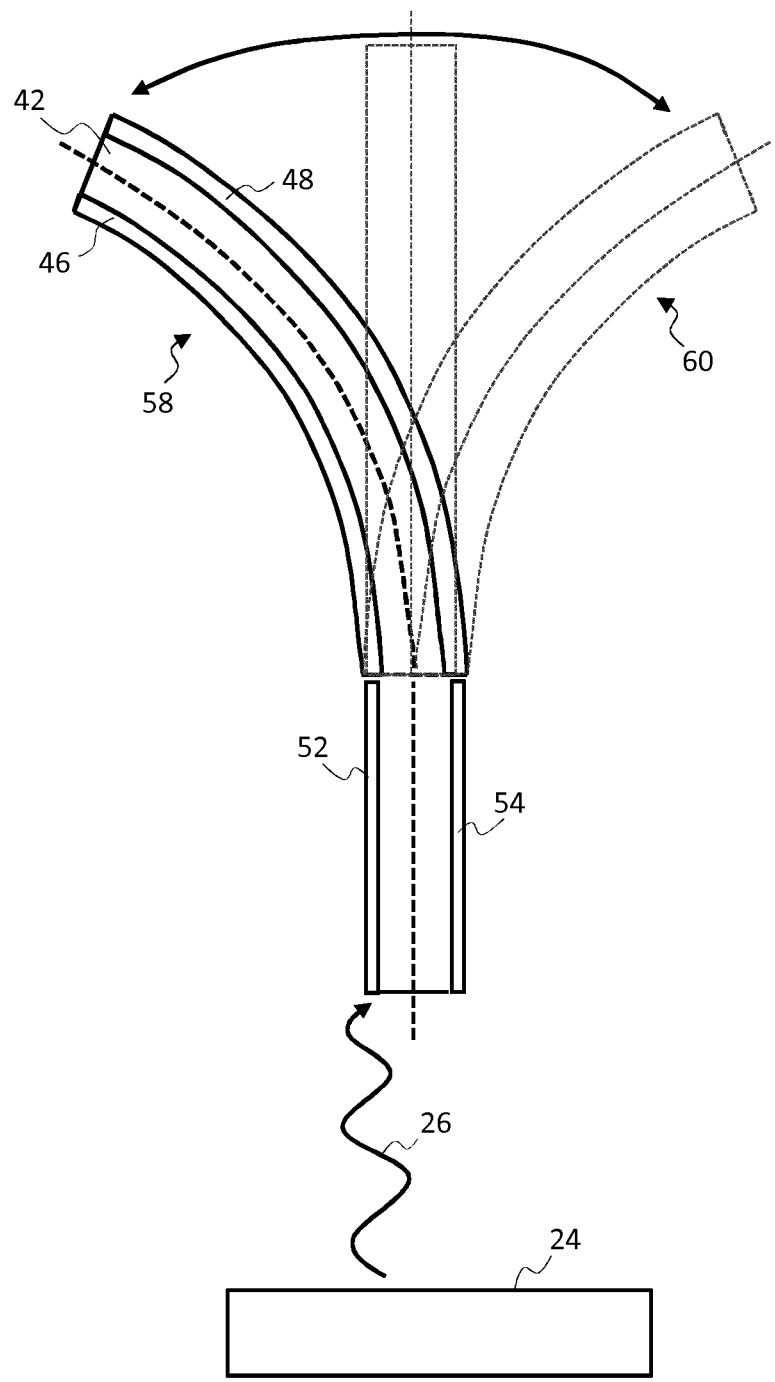
FIG. 6 schematically illustrates a catheter comprising one or more example actuator devices in accordance with one or more embodiments.

FIG. 6 illustrates the simple first example actuator device of FIG. 3 as implemented within a catheter 42 for providing an enhanced steering function for a steerable tip of the catheter. The catheter 42 comprises a pair of mutually opposing actuator members 46, 48, mounted along opposing wall sections of the lumen of tip of the catheter. Each of the two opposing actuator members is supplied with a separate light guide 52, 54, for optically coupling the respective actuator member with a single light source 24 located at a proximal end of the catheter. The light guides may in particular examples be optical fibres.

It is noted that dimensions in the schematic illustration of FIG. 6 are not drawn to scale. Although the light guides 52, 54 are drawn shorter than the actuator members 46, 48, in reality the light guides may extend along the entire length of the catheter to an ultimate proximal end. Furthermore, the light source 24 is shown as spatially separated from a proximal end of the catheter, however in practice the light guide may be mechanically (and optically) coupled to the end of the catheter, either permanently or removably.

The catheter application illustrated in FIG. 6 is aimed at solving a problem which presently pertains for multidirectional catheter tip steering, wherein mutually opposing (antagonistic) actuators installed in catheters for facilitating bidirectional steering hinder one another's actuation effect due to their residual stiffness which persists even when they are not active. In the ideal case, the mechanically active one of the actuators will be relatively stiff while actuating, so as to exert the greatest magnitude of force, while the mechanically passive of the two actuators would be relatively flexible, so as to offer the minimum possible resistance to the active actuator.

Accordingly, in the embodiment shown in FIG. 6, the controller (not shown) is configured to implement a reciprocal control regime wherein the two actuator members are controlled so as to have opposing stiffness levels: whenever one of the two actuator members 46, 48 is controlled to have a relatively high stiffness, the other of the two actuator members is controlled to have a relatively low stiffness (or even a minimal stiffness). In particular, the controller may be configured to determine which, if any, of the two actuator members is in an active actuation state, and to control this actuator member to have a relatively high stiffness level, while simultaneously controlling the other of the two actuator members to have a relatively low stiffness level.

This is illustrated in FIG. 6. When the first actuator member 46 is in an active actuation state, the catheter 42 is induced to steer to a (leftward) first position 58. In this actuation state, the controller is configured to control the first actuator member 46 to be in a relatively high stiffness state, and to control the second actuator member 48 to be in a relatively low stiffness state. On the contrary, when the second actuator member 48 is in an active actuation state, the catheter 42 is induced to steer to a (rightward) second position 60. In this actuation state, the controller is configured to control the second actuator member 48 to be in a relatively high stiffness state and to control the first actuator member 46 to be in a relatively low stiffness state.

Separate control of the two actuator members 46, 48 may be achieved in examples by providing two separate light sources 24 rather than the single light source illustrated in FIG. 6. Alternatively, the single light source shown in FIG. 6 may be adapted to have to independently controllable light output areas, one optically coupled with a proximal end of the first light guide 52 and the other optically coupled with a proximal end of the second light guide 54. Alternatively again, independent control of the two actuator members may be achieved by providing actuator members 46, 48, each comprising light-sensitive filler elements sensitive to different respective ranges of light wavelengths. In this way a single light source 26 may independently control both actuator members 46, 48 by selectively controlling the light output 26 to comprise only those wavelengths of light to which the actuator member-to-be-addressed is sensitive.

As noted above, controllable stiffness of an actuator member enables more complex and sophisticated actuation movements and shapes to be achieved in example embodiments. One particular application which would benefit from enhanced range of deformation actions is the navigation of catheters and guide-wires through narrow and tortuous (peripheral) blood vessels. Such navigation requires sophisticated steering technology, which can be difficult to achieve using standard EAP actuators having a fixed stiffness profile. Most effective steering is typically achieved by providing locally flexible regions in the EAP actuator located around the steering pivot points. Where these points are fixed, the intricacy and adaptability of the available steering motions is limited.

Examples in accordance with at least one set of embodiments therefore provide an elongate EAP actuator member having a plurality of 'soft-spots' located at various points along the length of the member, comprising local concentrations of light-absorbing filler elements to enable adjustment of a local stiffness level. The filler elements populating each 'soft-spot' are adapted to be sensitive to a different range of wavelengths, such that the stiffness of each local spot may be independently controlled.

Figure 7:
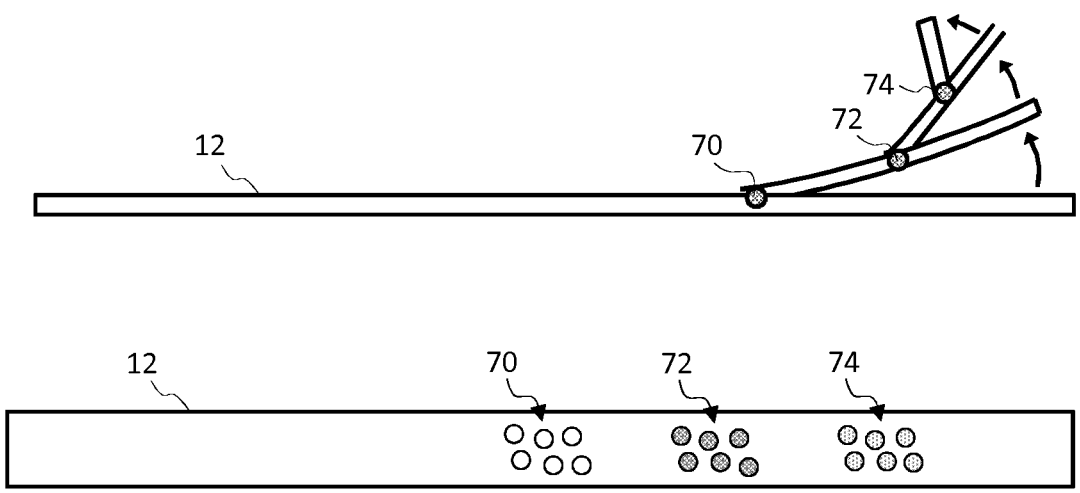
FIG. 7 schematically illustrates an actuator member of a third example actuator device in accordance with one or more embodiments.

An example is illustrated in FIG. 7, which shows an elongate actuator member 12 having three localised regions of light-absorptive filler elements 70, 72, 74, each comprising a local concentration of filler particles being adapted to absorb light of a different range of frequencies (or wavelengths). As shown in the upper image of FIG. 7, each localised region 70, 72, 74 forms a locally adjustable spot or point along the length of the actuator member. Upon luminous stimulation, each spot becomes flexible and effectively provides a local pivot point about which the actuator member 12 naturally bends upon deformation of the EAP material. By selectively stimulating one or more of the local regions 70, 72, 74 with the particular frequency (or frequencies) of light to which they are sensitive, a corresponding set one or more local steering pivot points may be spontaneously generated. In this way, the controller (not shown) is operable to selectively control the particular mode and shape of the actuator member steering which is achieved.

Although the particular example of FIG. 7 shows a set of only three local 'soft-spots' 70, 72, 74, in further examples, a greater number of local concentrations of filler particles may be provided; for example 10 or more, or even 20 or more. The greater the number of filler particles clusters, the greater the degree of control which is possible of the stiffness profile of the member 12 and therefore of the steering configuration. Embodiments according to the above examples enable adaptive steering functionality without use of complex geometrical structures of multiple EAP members or use of segmented EAP structures, both of which are complex to construct and operate, and also more expensive to fabricate.

In accordance with one or more further embodiments, there may be provided a guide-wire for blood vessel navigation and occlusion penetration comprising one or more actuator members in accordance with the invention. The actuator members may be for facilitating adjustable steering action of a tip of the guide-wire. The guide-wire tip may in particular be controllable to adjust between different flexibility states in accordance with a particular mode of operation. These modes may include for instance: straight navigation mode, steering navigation mode, and occlusion penetration mode.

Typically, in Chronic Total Occlusion removal procedures for instance, different guide-wires with different stiffnesses are used for different parts of the removal procedure. A relatively flexible guide-wire having medium-level stiffness may typically be used for quick and easy navigation in main blood vessels, a relatively soft guide-wire for manoeuvring in small and tortuous vessels, and finally a stiff guide-wire (tip) for penetration of the occlusion. By providing a guide-wire having a tip with adjustable stiffness levels, use of multiple different guide-wires may be avoided, significantly improving the efficiency and speed of the removal operation.

Figure 8:
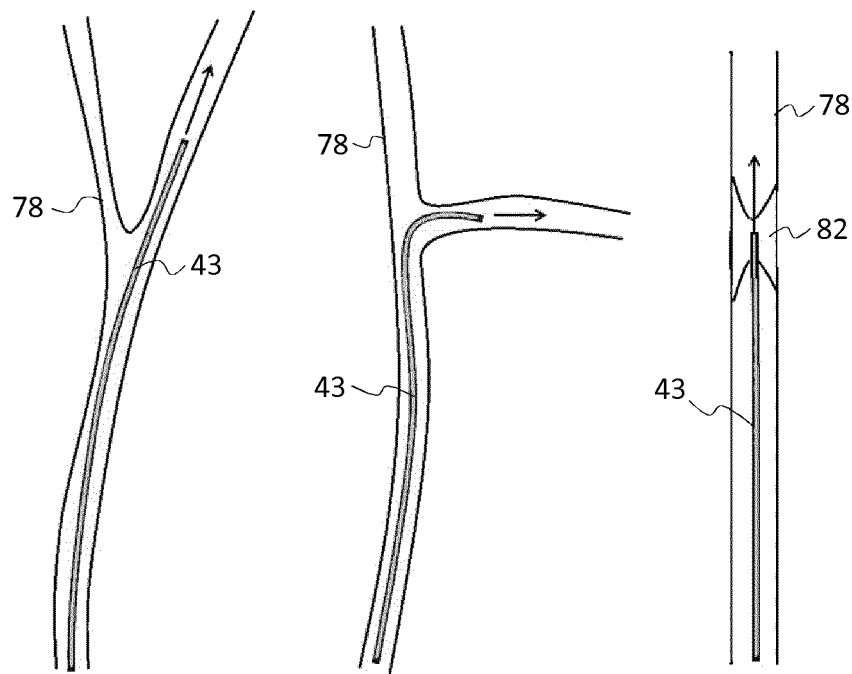
FIG. 8 schematically illustrates a guide wire comprising an example actuator device in accordance with one or more embodiments of the invention.

This is illustrated with greater clarity in FIG. 8 which shows an example guide-wire 43 having a steerable tip comprising at least one actuator member in accordance with an embodiment of the invention. The guide-wire is shown as implemented in three different modes of operation and control.

In the first mode (FIG. 8, left), an actuator member in the guide-wire tip is controlled (by means of an associated controllable light source—not shown in FIG. 8) to exhibit a low stiffness level, such that the guide-wire may be navigated through a relatively straight section of a blood vessel 78.

In the second mode (FIG. 8, centre), the actuator member in the guide-wire 43 tip is controlled to exhibit a medium level stiffness for navigating through a more tortuous section of a blood vessel 78. In this mode, the guide-wire tip is required to steer in one or more directions (by electrical stimulation of the EAP actuator). A relatively stiffer state is therefore preferred, for providing greater actuation force to facilitate the steering.

In a third mode (FIG. 8, right), the actuator member in the guide-wire 78 tip is controlled to exhibit a relatively high stiffness level, for penetrating a local occlusion (or stenosis) 82 in the blood vessel 78.

The actuator member may be readily varied between (at least) three different levels of stiffness by for example controlling an intensity of light directed onto the actuator member by an associated light source (not shown in FIG. 8).

Figure 9:
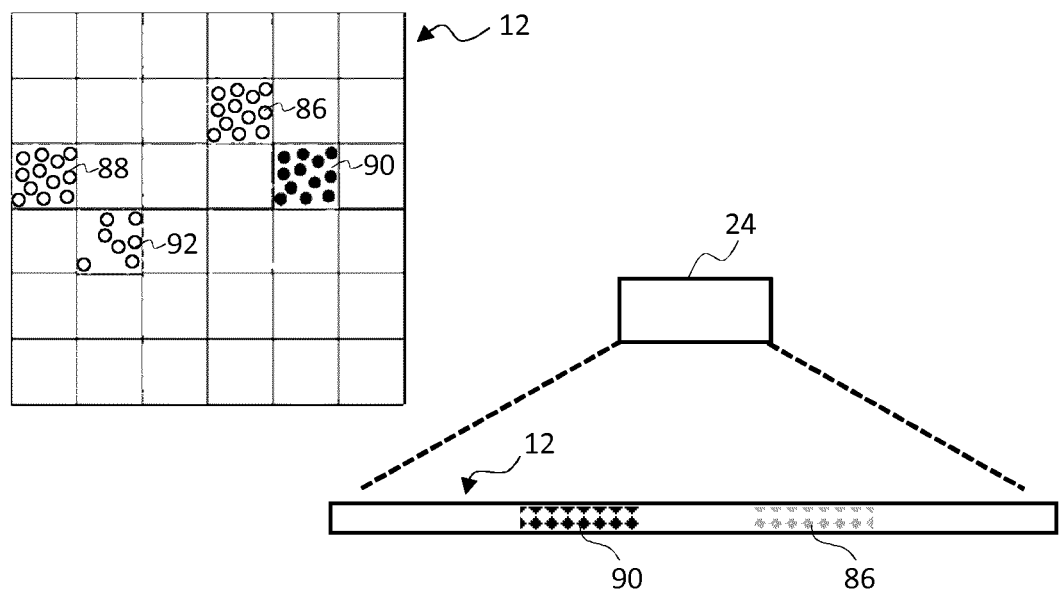
FIG. 9 schematically illustrates an actuator member of the fourth example actuator device in accordance with one or more embodiments of the invention.

FIG. 9 schematically illustrates a further example actuator device in accordance with one or more embodiments of the invention. The device includes an actuator member 12 formed of a single sheet of electroactive polymer material having a plurality of local concentrations 86, 88, 90, 92, of light absorbing filler elements of differing densities situated at a variety of different locations across the sheet. By varying the intensity and/or spectral composition of the light output provided onto the actuator member 12 by the light source 24, different local deformation behaviours can be induced at the various locations upon electrical stimulation of the EAP material. In particular, by selectively controlling the relative stiffness of the different localised areas, a different stiffness profile may be realised across the actuator member 12, and consequently, upon deformation of the actuator member, different bending and compression shapes and effects induced.

In accordance with one or more examples, the light absorbing filler elements of two or more of the different localised regions may be selected so as to be sensitive to different respective ranges of light wavelengths. In this way, independent selective control of different of the local regions may be achieved by means of a single light source 24 (by selectively controlling the particular wavelengths of light comprised within the light output generated by the light source).

Examples in accordance with this embodiment may be used to create actuation array effects without the use of complex EAP structuring, arrays, or matrix driving. This may be potentially useful for instance in simple (haptic) user interfaces and optical devices.

Examples in accordance with a further set of embodiments may provide an actuator member formed of a punctured sheet of EAP compound material having puncture holes (or pores) whose size which is controllable in dependence upon the intensity and/or spectral composition of an applied luminous stimulus. Such a punctured sheet may provide a membrane for enabling controlled diffusion for example.

For example, the actuator member sheet may delimit a plurality of openings, wherein each opening is surrounded by, or in mechanical communication with, a region of EAP material having light absorbing filler elements adapted to be sensitive to light of a particular set of one or more frequencies. Certain subsets of the openings may have filler elements adapted to be sensitive to a common set of one of more frequencies. Each opening may alternatively be provided filler elements adapted to be sensitive to a unique set of one or more frequencies.

The actuator member sheet may be adapted such that, in the absence of any applied electrical stimulus to the EAP, all of the openings are open (or alternatively all of the openings are closed). Upon stimulation of the EAP with an electrical stimulus, the actuator member sheet may be adapted to deform in such a way that all of the openings switch to being closed (or open). It can be appreciated that by varying the stiffness of regions of the actuator member sheet immediately surrounding specific sets of one or more of the openings, said openings may be controlled to respond in a different way to either absence or application of the electrical stimulus. By optically stimulating certain openings therefore (with light of a spectral composition to which they are sensitive) particular openings may be controlled for instance to open when remaining holes are closed or to close (when remaining holes are open. In this way, individual (sets of one or more) openings may be independently controlled.

Hence, by suitably combining electrical and optical stimuli, custom control over the particular number and pattern of openings which are open at any one time may be achieved, as well as, in particular examples, control over the size of each of the open holes (for instance through varying an intensity of the various spectral components of the luminous stimulus).

Where different subsets of one or more holes have surrounding or adjacent filler elements sensitive to different wavelengths of light, by controlling the spectral composition of the applied luminous stimulus, it is possible to control the particular configuration of holes that are open at any one time (i.e. by selectively including or excluding the wavelengths known to be associated with different subsets).

Such an embodiment may be used as a membrane providing controlled diffusion across its surface, in particular by selectively controlling a greater or lesser number of the openings to be open or closed at any one time.

In accordance with one or more particular examples, a direction of diffusion may also be controlled. This may be achieved for instance by means of a membrane having surfaces or surface regions which point in a range of different directions. This might include a curved membrane (either a closed curve such as a sphere, or an open curve), or a jointed membrane having plural planar surfaces facing in different directions. By selectively controlling the number of holes open across each of the differently facing surfaces or surface sections, the rate of diffusion in each of the different directions may be controlled.

In accordance with one or more embodiments of the invention, an actuator member may be provided comprising light absorbing filler elements which are composed at least partially of a material having a temperature-dependent optical transmittance. In particular, the optical transmittance may be adapted or selected so as to stabilise or plateau upon reaching a particular temperature. More specifically, the optical transmittance may be controlled to stabilise or plateau for temperatures above a glass transition temperature $T_g$ of the electroactive polymer material comprised by the actuator member.

The stiffness of a polymer makes a sharp drop close to the glass transition temperature $T_g$. At this temperature, it becomes very difficult to control the exact stiffness of the material. By incorporating particles of a material having a changing optical transmittance at a certain temperature (e.g. at a melting temperature of the particles or at a trans to cis transition temperature for Azo containing polymers (see below)), stable control over the stiffness may be achieved. In particular if a material is selected having an optical transmittance which plateaus or levels out above said certain temperature, further heating of the actuator member once that particular temperature is exceeded becomes increasingly more difficult. As a result, the temperature of the actuator member stabilises, and consequently control over the stiffness level of the material may be retained.

Figure 10:
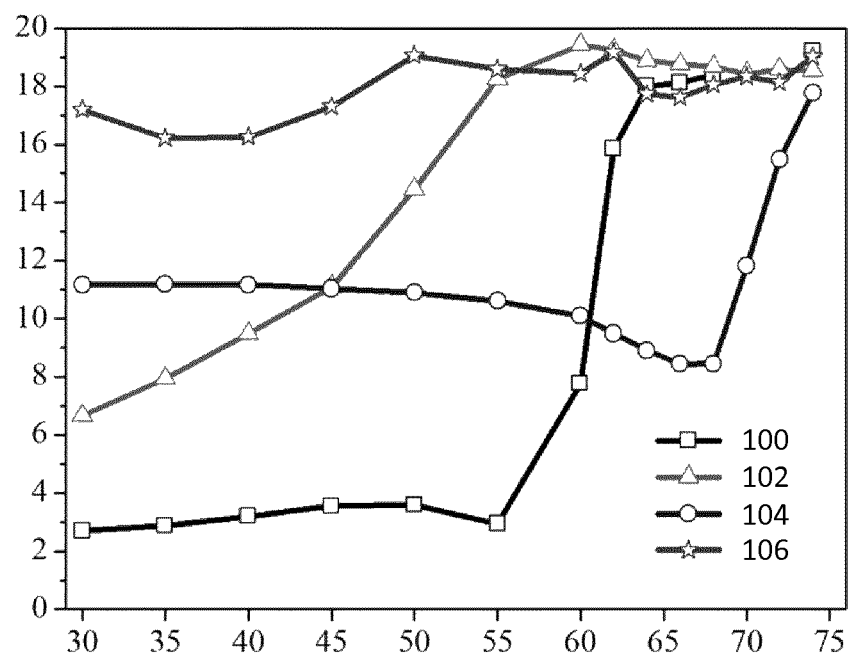
FIG. 10 shows a graph illustrating a relationship between optical transmittance and temperature for a number of different polymers.

The effect is illustrated in particular for Azo containing polymer fillers in FIG. 10, which shows a graph of optical transmittance (y-axis, arbitrary units) against temperature (x-axis, ° C.) for a number of different example polymer filler materials. The different trend lines 100, 102, 104, 106 represent different AZO compounds.

Certain of the materials exhibit the plateau-like behaviour described above, and would therefore be particularly suitable candidates for inclusion as light absorbing filler elements in embodiments of the invention. In particular, material 100 exhibits a particularly sharp transition in optical transmittance at approximately 55° C., before levelling off at approximately 64° C. This may be a particularly suitable candidate material therefore. Material 102 exhibits a similar, although weaker, transmittance behaviour, increasing relatively steadily between 30° C. and approximately 60° C., before levelling off at a similar transmittance level to material 100.

By contrast, material 104 exhibits the sharp spike in transmittance (at approximately 68° C.) which characterises material 100, but does not plateau at a given higher temperature, but continues on an upward trend. This material may therefore be less preferable. Material 104 also may be less preferable, exhibiting a roughly uniform optical transmittance between the range 30° C. and 75° C.

In accordance with one or more embodiments, further control over stiffness of an EAP actuator member may be achieved through the melting of the light absorbing filler elements. When an electroactive polymer is provided with filler elements or particles or fibres, the stiffness of the overall composite material will change upon melting of the particles (even if the stiffness of the electroactive polymer material itself remains unchanged). This then provides a further means for (at least uniformly) adjusting a stiffness level of such an electroactive polymer actuator member. Additionally, if the filler particles are (semi-)crystalline, the optical transmission spectra will also change when the particles melt. Temperature dependent optical properties of the sort described in the embodiment outlined above may then also be achieved in accordance with these examples.

Figure 11:
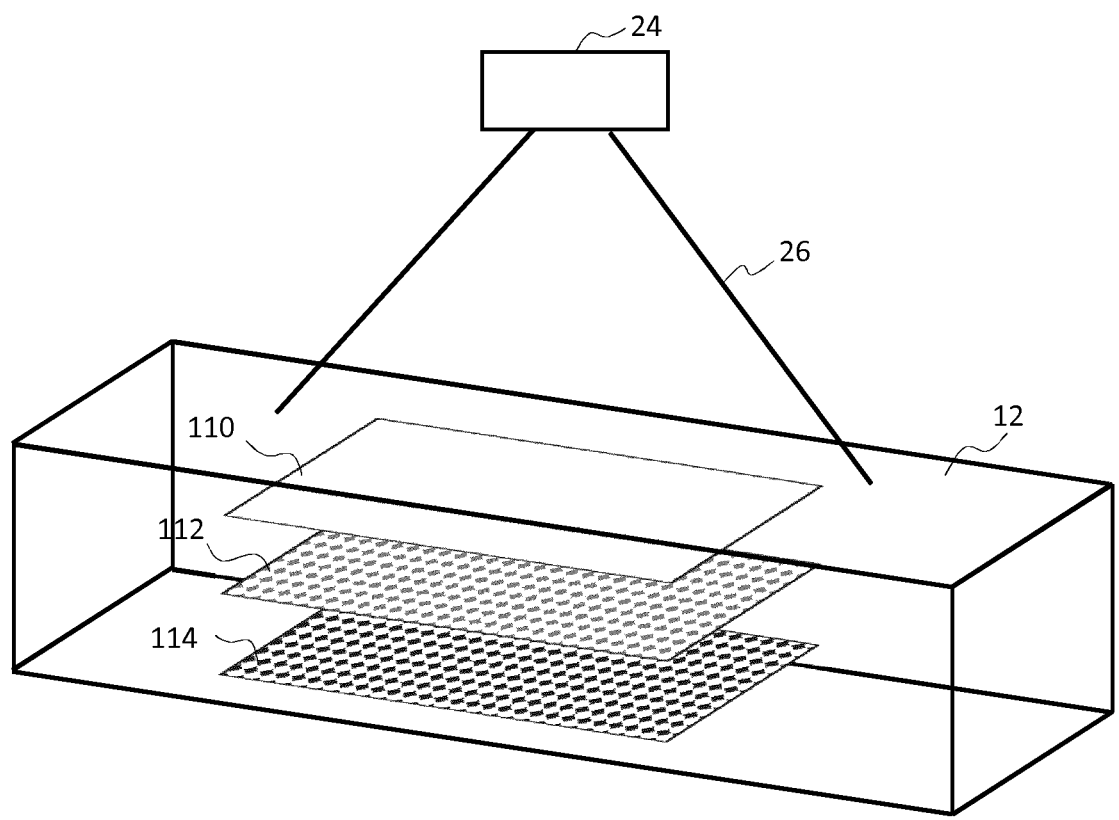
FIG. 11 schematically illustrates an actuator member of a fifth example actuator device in accordance with one or more embodiments of the invention.

A further example actuator device in accordance with one or more embodiments of the invention is illustrated in FIG. 11. The device comprises an actuator member 12 having a stacked set of three planar arrangements of light absorbing filler elements 110, 112, 114, each planar arrangement comprising filler elements adapted to absorb light of a different set or range of wavelengths. In particular, the three planar arrangements of particles are selected so as to be absorptive of so-called subtractive colours (cyan, magenta, yellow) which comprise a typical white light source. The three planar arrangements are stacked along an axis extending parallel to an optical axis of light outputs 26 being directed onto the actuator member 12 by a light source 24.

Each of the stacked arrangements of filler elements is adapted to absorb one portion of the spectral composition of the light output 26, and to transmit the remaining portions. In this way, light directed onto the stack of planar filler element arrangements is successively 'stripped' of different wavelengths of light as it passes through each of the different layers. The arrangement provides a means of selectively controlling a local stiffness level of the actuator member in a direction parallel with the optical axis of the incident light (i.e. within the thickness of the actuator member).

In examples, the light absorbing filler elements populating the various planar arrangements may comprise different dyes or may for instance comprise different varieties of phosphor.

The composition of the light could be adjusted in accordance with which of the layers are desired to be stimulated. For example the light source may comprise only cyan and yellow light so that the middle layer is not stimulated.

In this way, selective heating of two or more local planar regions stacked atop one another may be achieved through illumination of only one side of the stack.

Although in the detailed description herein above, the construction and operation of devices and systems according to the invention have been described for EAPs, the invention can in fact be used for devices based on other kinds of EAM (electro-active material). Hence, unless indicated otherwise, the EAP materials hereinabove can be replaced with other EAM materials. Such other EAM materials are known in the art and the person skilled in the art will know where to find them and how to apply them. A number of options will be described herein below.

Field driven EAMs can be organic or inorganic materials and if organic can be single molecule, oligomeric or polymeric. They are generally piezoelectric and possibly ferroelectric and thus comprise a spontaneous permanent polarization (dipole moment). Alternatively, they are electrostrictive and thus comprise only a polarization (dipole moment) when driven, but not when not driven. Alternatively they are dielectric relaxor materials. Such polymers include, but are not limited to, the sub-classes: piezoelectric polymers, ferroelectric polymers, electrostrictive polymers, relaxor ferroelectric polymers (such as PVDF based relaxor polymers or polyurethanes), dielectric elastomers, liquid crystal elastomers. Other examples include electrostrictive graft polymers, electrostrictive paper, electrets, electroviscoelastic elastomers and liquid crystal elastomers.

The lack of a spontaneous polarization means that electrostrictive polymers display little or no hysteretic loss even at very high frequencies of operation. The advantages are however gained at the expense of temperature stability. Relaxors operate best in situations where the temperature can be stabilized to within approximately 10° C. This may seem extremely limiting at first glance, but given that electrostrictors excel at high frequencies and very low driving fields, then the applications tend to be in specialized micro actuators. Temperature stabilization of such small devices is relatively simple and often presents only a minor problem in the overall design and development process.

Relaxor ferroelectric materials can have an electrostrictive constant that is high enough for good practical use, i.e. advantageous for simultaneous sensing and actuation functions. Relaxor ferroelectric materials are non-ferroelectric when zero driving field (i.e. voltage) is applied to them, but become ferroelectric during driving. Hence there is no electromechanical coupling present in the material at non-driving. The electromechanical coupling becomes non-zero when a drive signal is applied and can be measured through applying the small amplitude high frequency signal on top of the drive signal, in accordance with the procedures described above. Relaxor ferroelectric materials, moreover, benefit from a unique combination of high electromechanical coupling at non-zero drive signal and good actuation characteristics.

The most commonly used examples of inorganic relaxor ferroelectric materials are: lead magnesium niobate (PMN), lead magnesium niobate-lead titanate (PMN-PT) and lead lanthanum zirconate titanate (PLZT). But others are known in the art.

PVDF based relaxor ferroelectric based polymers show spontaneous electric polarization and they can be pre-strained for improved performance in the strained direction. They can be any one chosen from the group of materials herein below.

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The current driven EAMs and EAPs comprise conjugated polymers, Ionic Polymer Metal Composites, ionic gels and polymer gels.

Examples of ionic-driven EAPs are conjugated polymers, carbon nanotube (CNT) polymer composites and Ionic Polymer Metal Composites (IPMC).

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

The materials above can be implanted as pure materials or as materials suspended in matrix materials. Matrix materials can comprise polymers.

To any actuation structure comprising EAM material, additional passive layers may be provided for influencing the behavior of the EAM layer in response to an applied drive signal.

The actuation arrangement or structure of an EAP device can have one or more electrodes for providing the control signal or drive signal to at least a part of the electroactive material. Preferably the arrangement comprises two electrodes. The EAP may be sandwiched between two or more electrodes. This sandwiching is needed for an actuator arrangement that comprises an elastomeric dielectric material, as its actuation is among others due to compressive force exerted by the electrodes attracting each other due to a drive signal. The two or more electrodes can also be embedded in the elastomeric dielectric material. Electrodes may be patterned or non-patterned.

A substrate can be part of the actuation arrangement. It can be attached to the ensemble of EAP and electrodes between the electrodes or to one of the electrodes on the outside.

The electrodes may be stretchable so that they follow the deformation of the EAM material layer. This is especially advantageous for EAP materials. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT: PSS). Metalized polyester films may also be used, such as metalized polyethylene terephthalate (PET), for example using an aluminum coating.

Some arrangements may have electrode layers on each side of the electroactive material layer. It is also possible to provide an electrode layer on one side only for example using interdigitated comb electrodes. If electrodes are on one side only, a reflective device may be formed without the need for transparent electrodes.

The materials for the different layers will be selected for example taking account of the elastic moduli (Young's moduli) of the different layers.

Additional layers to those discussed above may be used to adapt the electrical or mechanical behavior of the device, such as additional polymer layers.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:
1. An actuator device comprising:
   an actuator member comprising:
      an electroactive material, wherein the electroactive material is arranged to deform in response to application of an electrical stimulus; and
      light absorbing filler elements disposed within the electroactive material, wherein the light absorbing filler elements are arranged to absorb and convert incident light energy to heat energy;
   a controllable light source,
      wherein the controllable light source is optically coupled to the actuator member,
      wherein the controllable light source is arranged to provide a light output onto the actuator member, and
      wherein the light output is controllable between a range of different intensity levels so as to controllably adjust a stiffness profile of the actuator member; and
   a controller circuit arranged to control an intensity level of the light output so as to selectively realize in the actuator member any of a range of at least three different stiffness profiles.

2. The actuator device as claimed in claim 1, wherein the controller circuit is arranged to control the intensity level of the light output so as to realize in at least a portion of the actuator member any of a continuous spectrum of stiffness levels.

3. The actuator device as claimed in claim 1, wherein the controller circuit is arranged to selectively control the stiffness profile realized in the actuator member on the basis of a pre-defined control schedule.

4. The actuator device as claimed in claim 1, wherein the light absorbing filler elements are non-homogenously distributed in the electroactive material, so as to enable realizing of spatially non-uniform stiffness profiles in the actuator member.

5. The actuator device as claimed in claim 4, wherein the light absorbing filler elements are distributed in a set of spatially discrete concentrations of filler elements.

6. The actuator device as claimed in claim 1,
   wherein the actuator member comprises a plurality of different locally concentrated groups of light absorbing filler elements,
   wherein each group of the plurality of different locally concentrated groups is arranged to absorb light of a different range of wavelengths, and
   wherein the controller circuit is arranged to control a spectral composition of the light output in accordance with a defined control schedule, in order to realize a particular stiffness profile of the actuator member.

7. The actuator device as claimed in claim 6, wherein the controller circuit is arranged to selectively control local stiffness of the actuator member at one or more regions of the actuator member by selectively including or excluding wavelengths of light to which filler elements are sensitive.

8. The actuator device as claimed in claim 6, comprising a stacked arrangement of multiple different planar concentrations of filler elements,
   wherein the filler elements are stacked along an axis extending parallel to an optical axis of the light output, and
   wherein each planar concentration of the multiple different planar concentrations is arranged to absorb a different portion of the spectral composition of the light output.

9. The actuator device as claimed in claim 1, wherein the controllable light source and the actuator member are optically coupled by means of an elongate light guide.

10. The actuator device as claimed in claim 1, wherein the light absorbing filler elements comprise filler elements formed of at least one of a black pigment, a transition metal, a wavelength-specific dye, a phosphor, and a fluorophore.

11. The actuator device as claimed in claim 1, wherein the light absorbing filler elements comprise a material having a temperature-dependent optical transmittance, such that optical transmittance plateaus at a particular temperature.

12. The actuator device as claimed in claim 11, wherein the optical transmittance plateaus for temperatures above a glass transition temperature of the electroactive material.

13. An elongate probe having a steerable section, the elongate probe comprising one or more of the actuator device claimed in claim 1 for facilitating steering of the steerable section.

14. The elongate probe as claimed in claim 13, comprising a pair of opposing actuator members for steering the steerable section, wherein a stiffness of the two opposing actuator members is reciprocally controlled such that upon steering in any given direction, a mechanically active one of the two opposing actuator members is controlled to have a high stiffness, for enabling a strong active actuation force, and a mechanically passive one of the two opposing actuator members is controlled to have a low stiffness, for ensuring minimum resistance to the actuation force.

15. The elongate probe as claimed in claim 13, further comprising a dedicated light guide for each actuator member wherein each actuator member provides a separately controllable light output.

16. The actuator device as claimed in claim 1,
wherein the light output is controllable between a range of different spectral compositions so as to controllably adjust the stiffness profile of the actuator member; and
wherein the controller circuit is arranged to control level spectral profile of the light output so as to selectively realize in the actuator member any of the range of at least three different stiffness profiles.

17. The actuator device as claimed in claim 16, wherein the controller circuit is arranged to control the level spectral profile of the light output so as to realize in at least a portion of the actuator member any of a continuous spectrum of stiffness levels.

18. The actuator device as claimed in claim 1, wherein the controller circuit is arranged to selectively control the stiffness profile realized in the actuator member on the basis of one or more input control parameters.

19. A method of selectively controlling a stiffness profile of an actuator member wherein the actuator member comprises an electroactive material, arranged to deform in response to application of an electrical stimulus, and light absorbing filler elements within the electroactive material, wherein the light absorbing filler elements are arranged to absorb and convert incident light energy to heat energy the method comprising:
directing a light output onto the actuator member, the light output having a controllable intensity level; and
controlling the intensity level of the light output so as to selectively realize in the actuator member any of a range of at least three different stiffness profiles.

20. The method of claim 19, further comprising controlling a spectral profile of the light output, wherein the light output has a controllable spectral composition.

* * * * *

UNITED STATES PATENT AND TRADEMARK OFFICE
CERTIFICATE OF CORRECTION

| | |
|---|---|
| PATENT NO. | : 10,680,162 B2 |
| APPLICATION NO. | : 16/347610 |
| DATED | : June 9, 2020 |
| INVENTOR(S) | : Pelssers et al. |

It is certified that error appears in the above-identified patent and that said Letters Patent is hereby corrected as shown below:

On the Title Page

Item (72), under Inventors, in Column 1, Lines 2-3, delete "Petrus Cornelis Hendriks," and insert -- Cornelis Petrus Hendriks, --, therefor.

In the Specification

In Column 2, Line 60, delete "polypyrolle (PPy)," and insert -- polypyrrole (PPy), --, therefor.

In Column 9, Lines 47-60, delete "The rigidity or stiffness........changes in elasticity." and insert the same at Line 48 as a new paragraph.

In Column 9, Line 52, delete "materials" and insert -- materials. --, therefor.

In Column 9, Line 62, delete "Celcius" and insert -- Celsius --, therefor.

In Column 13, Line 33, delete "printing)" and insert -- printing). --, therefor.

In Column 13, Line 36, delete "Piezo electric" and insert -- Piezoelectric --, therefor.

In Column 13, Lines 64-65, delete "P(VDFTrFE)" and insert -- P(VDF-TrFE) --, therefor.

In Column 15, Lines 55-56, delete "light source 26." and insert -- light source 24. --, therefor.

In Column 17, Line 2, delete "light source 26" and insert -- light source 24 --, therefor.

In Column 17, Line 43, delete "one or" and insert -- of one or --, therefor.

In Column 18, Line 38, delete "guide-wire 78" and insert -- guide-wire 43 --, therefor.

Signed and Sealed this
Twelfth Day of January, 2021

Andrei Iancu
*Director of the United States Patent and Trademark Office*

CERTIFICATE OF CORRECTION (continued)
U.S. Pat. No. 10,680,162 B2

In Column 19, Line 23, delete "one of" and insert -- one or --, therefor.

In the Claims

In Column 25, Line 6, in Claim 15, delete "member" and insert -- member, --, therefor.

In Column 26, Line 6, in Claim 19, delete "member" and insert -- member, --, therefor.

In Column 26, Line 7, in Claim 19, delete "material," and insert -- material --, therefor.

In Column 26, Line 11, in Claim 19, delete "energy" and insert -- energy, --, therefor.